(12) United States Patent
Shepodd

(10) Patent No.: US 6,472,443 B1
(45) Date of Patent: Oct. 29, 2002

(54) POROUS POLYMER MEDIA

(75) Inventor: Timothy J. Shepodd, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 29 days.

(21) Appl. No.: 09/603,466

(22) Filed: Jun. 22, 2000

(51) Int. Cl.⁷ .................................................. C08J 9/28
(52) U.S. Cl. ............................ 521/63; 521/62; 521/64; 521/142; 521/149; 521/150; 521/152; 521/182; 521/183; 521/185; 428/304.4; 428/313.5; 428/317.1
(58) Field of Search .............................. 521/62, 63, 64, 521/142, 149, 150, 152, 182, 183, 185; 428/304.4, 313.5, 317.1

(56) References Cited

U.S. PATENT DOCUMENTS 4,952,651 A * 8/1990 Kasai et al. .................. 521/64
5,428,067 A * 6/1995 Wulff et al. .................. 521/54

OTHER PUBLICATIONS

Palm, A. and Novotny, M., *Analytical Chem.*, 69, 4499–4507, Nov. 15, 1997.
Ericson, C., et al., *Analytical Chem.*, 72, 81–87, Jan. 1, 2000.

* cited by examiner

*Primary Examiner*—John M. Cooney, Jr.
(74) *Attorney, Agent, or Firm*—Donald A. Nissen

(57) ABSTRACT

Highly crosslinked monolithic porous polymer materials for chromatographic applications. By using solvent compositions that provide not only for polymerization of acrylate monomers in such a fashion that a porous polymer network is formed prior to phase separation but also for exchanging the polymerization solvent for a running buffer using electroosmotic flow, the need for high pressure purging is eliminated. The polymer materials have been shown to be an effective capillary electrochromatographic separations medium at lower field strengths than conventional polymer media. Further, because of their highly crosslinked nature these polymer materials are structurally stable in a wide range of organic and aqueous solvents and over a pH range of 2–12.

10 Claims, 2 Drawing Sheets

1. Thiourea
2. Benzyl alcohol
3. Benzamide
4. Benzene
5. Benzophenone
6. Toluene
7. Ethylbenzene
8. Fluoranthene

POROUS POLYMER MEDIA

STATEMENT OF GOVERNMENT INTEREST

This invention was made with Government support under contract no. E-AC04-94AL85000 awarded by the U.S. Department of Energy to Sandia Corporation. The Government has certain rights in the invention.

CROSS-REFERENCE TO RELATED APPLICATIONS

Not applicable.

BACKGROUND OF THE INVENTION

The present invention is directed to polymer and solvent compositions and methods pertaining thereto that provide for the formation of a highly table porous polymer network prior to phase separation and for electroosmotic exchange of the polymerization solvent, thereby eliminating the need for high pressure purging.

Monolithic polymeric materials composed of polymerized monomers (styrenes, acrylates, methacrylates, etc.) have proven useful as the stationary phase for various chromatographic applications and particularly for applications involving miniaturized or capillary columns where traditional methods of column packing have proven to be ineffective. Thus, porous stationary phase materials that are "cast-in-place" or "cast-to-shape by polymerization of mixtures of monomers directly within the confines of a chromatographic column, such as those disclosed in U.S. Pat. No. 5,728,457 entitled "Porous Polymer Material with Gradients" and issued to Frechet et al. on Mar. 7, 1998, have been developed to address this problem. By careful control of polymerization rate, time, and temperature Frechet has produced a single molded polymer monolith that possesses desirable hydrodynamic properties by virtue of being traversed by large channels and permeated by small pores. Several variations have already been successfully used in the separation of polyaromatic hydrocarbons (PAH), PTH-labeled amino acids, peptides, and explosives.

In phase-separation polymerization, a solution of monomers is polymerized. When the polymer molecules grow sufficiently large, they separate from the inert solvent (phase separate). A liquid-liquid or liquid-solid phase separation can occur with partitioning of the unreacted monomers. If a three-dimensional network is formed before precipitation, a polymer monolith consisting of a three-dimensional network of solid polymer and an interconnected network of solvent filled pores will be formed. The structure and dimensions of the interconnected porous polymer network can be determined by controlling the proportions of solvent as well as the monomer and solvent composition.

Prior to using a polymer monolith as a chromatography separation medium or as the dielectric medium for electrokinetic pumping applications it is generally necessary to remove the polymerization solvent. Prior art processes have required the use of high pressure purging schemes to remove the polymerization solvent. Attempts to employ electric field induced flow, such as electroosmotic flow (EOF) have been unsatisfactory because prior art phase separated polymer monoliths have been cast in solvents, such as water, that because of their low conductivity do not support EOF that is large enough to purge the solvent from the polymer monolith within a reasonable period of time. Consequently, it has been necessary to laboriously purge the polymerization solvent by application of pressure to force a fluid, such as a running buffer, through the porous network. However, as the size of capillary channels is reduced and/or the cell size of the polymer stationary phase material decreases this option becomes untenable. Pressure cannot be used to purge small cell size polymer monoliths because the pressures needed for practical flow rates are typically higher than the bulk moduli of the polymer media. Thus, attempts at pressure purging small cell size polymer monoliths can result in failure of the bulk matrix or insufficient flow to exchange out the polymerization solvent in a reasonable time. Thus, it would be desirable, and in fact necessary, as capillary dimensions and cell sizes become smaller, to remove residual polymerization solvent by means other than by the use of high pressure purging.

Recognizing the advantage of being able to purge solvent from the polymer material by the use of EOF, Palm et al., Anal. Chem., 69, 4499–4507, 1997, have described a one-step process for in situ preparation of macroporous polyacrylamide gel matrices for capillary electrochromatography that can be purged by EOF. While the solvent can be purged from these formulations by the use of EOF, the gel matrices have limited stability in useful chromatographic solvents such as acetonitrile; being stable only up to about 50% acetonitrile. Moreover, polyacrylamide gels are highly swelled gels of low polymer content that rely on the swelling solvent for their structure. Thus, these gels suffer from the drawback that they cannot be dehydrated without losing their structure.

It is possible to increase the ionic conductivity of an aqueous polymerization solvent by adding salts, etc., however, to do so can change the solubility of the monomers used as well as the nature and structure of the polymer phase formed upon phase separation. Further, in order for the polymer monolith to support electric field induced EOF it is necessary to incorporate a small amount of charged monomers in the formulation. What is needed is not only a polymerization solvent that possesses sufficient ionic conductivity that it can be removed by EOF within a reasonable period of time but also a monomer or combination of monomers that will polymerize in the presence of this polymerization solvent to form a three-dimensional polymer network prior to phase separation. Further, it is necessary that this three-dimensional polymer network provide sufficient surface charge density to support EOF.

As discussed above, applications for porous monolithic polymer materials range from the stationary phase in various chromatographic applications such as electrochromatography to providing the dielectric medium for electrokinetic pumping. These applications can employ a wide range of organic as well as inorganic solutions as the mobile phase. The composition of the mobile phase that can range, by way of example, from 100% acetonitrile to aqueous solutions having a pH anywhere in the range of 2–12, and mixtures thereof. Thus, in addition to being able to support EOF, it is necessary that the polymer monolith possess a high degree of stability, which is defined as resistance to swelling, dissolution and/or structure change in a wide range of mobile phase solutions.

SUMMARY OF THE INVENTION

The present invention is directed to polymer and solvent compositions and methods pertaining thereto that provide for the formation of a highly stable porous polymer network prior to phase separation and for electroosmotic exchange of the polymerization solvent following the step of polymerization, thereby eliminating the need for high pressure purging. Because they can be rapidly cured from low-viscosity acrylate monomer solutions under UV radiation (typically in less than 30 minutes) the porous polymer monoliths of the invention provide for easy manufacturability and for ease of placement into microchannels. Further, because they readily support electroosmotic flow (EOF), the polymerization solvents can be easily exchanged for a chromatography mobile phase without the need for pressurized flow. Moreover, because they are covalently bound to a substrate, the porous polymer monoliths can withstand high pressures without being extruded from the substrate.

The monomer mixtures of the invention contain a relatively high proportion of a crosslinking material (generally≈30 vol %). Extensive crosslinking allows the porous polymer monoliths to achieve high molecular weights and, in contrast to prior art porous polymer materials imparts a high structural stability such that the polymer monolith resists swelling and/or dissolution in the presence of a wide variety of solvents.

Thus, it is an object of this invention to provide a porous polymer material that can be purged of polymerization solvent by the use of EOF.

It is another object of the invention to provide a class of polymerization solvents that posses sufficient conductivity that they can be removed from the porous polymer matrix by EOF.

It is a further object of the invention to provide a polymerization process that operates to produce a porous polymer matrix in the presence of conductive polymerization solvents.

Yet another object of the invention is to provide a stable porous polymer matrix that resists swelling and/or dissolution in a wide range of organic and aqueous liquids.

These and other objects of this invention will become apparent from the description below and accompanying drawings.

DETAILED DESCRIPTION OF THE INVENTION

Figure 1:
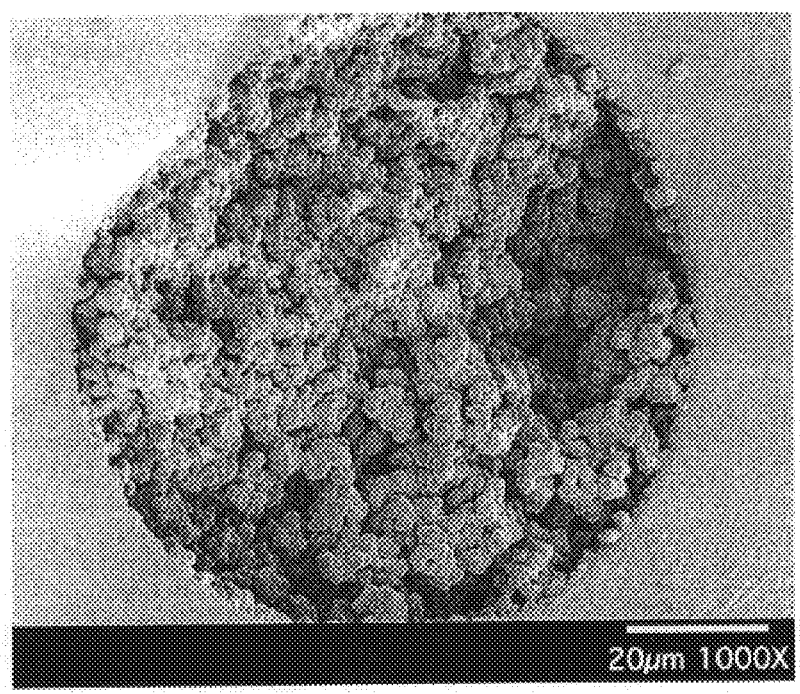
FIG. 1 is a scanning electron micrograph showing the microstructure of a polymer material produced by the invention.

The polymeric material of the present invention is a cast-to-shape, 3-dimensional structure that can be polymerized by phase separation inside a chromatography column or micromachined groove to form a highly crosslinked, very stable polymer material that possesses unique properties. These properties make this material especially suitable as the stationary phase for chromatographic applications, including capillary electrochromatography, and as the dielectric medium for electrokinetic pumping applications. Included among these properties are: 1) an interconnected 3-dimensional polymer network that provides a high internal volume and easy access to the interior and thus high permeability for fluids; 2) a polymer surface containing charged groups that support electroosmotic flow (EOF), generally provided by bifunctional monomers selected from the group including sulfonates, phosphonates, and boronates and ammonium compounds containing active vinyl groups in the molecule; 3) a polymerization solvent that not only provides for phase separation polymerization but also possesses sufficient ionic conductivity that it can be removed using electroosmotic flow, in contrast to prior art polymerization solvents which require high pressure pumping; and 4) resistance to structural degradation in a wide variety of aqueous and organic solvents and mixtures thereof as well as air drying.

If a solid immersed in a liquid can become charged, either through adsorption of ions from the solution or by virtue of the nature of the surface of the solid, i.e., the surface inherently contains charged species, an electrically charged layer (electric double layer) will exist at the solid/liquid interface. The application of electrodes to produce an in-situ electric field, results in the displacement of the mobile charged layer with respect to the stationary charged surface layer; the golid phase being fixed while the liquid is free to move. Providing the liquid phase possesses some degree of ionic conductivity, the liquid will tend to flow or be pumped through the pores of the solid phase to produce electroosmotic flow. The direction the liquid moves is dependent upon the sign of the charge it carries with respect to that of the solid and the velocity with which the liquid moves has been shown to be dependent upon the magnitude of the electric field. A more complete discussion of this effect can be found in prior now abandoned application Ser. No. 09/310465, filed May 11, 1999 and entitled "Castable Three-Dimensional Stationary Phase for Chromatography", and copending continuation-in-part application Ser. No. 09/796, 762 filled Apr. 28, 2001 incorporated herein by reference in its entirety. Thus, for applications that depend upon electroosmotic flow through a stationary phase, it is necessary not only to have a porous stationary phase that possesses a microstructure capable of efficient hydrodynamic flow but also a surface charge density on the microstructure sufficient to promote electroosmotic flow. It is further necessary to have a liquid phase that possesses a high enough ionic conductivity that a reasonable fluid flowrate can be maintained. The present invention provides a polymer monolith, produced by a phase separation process, that possesses a porous microstructure having a charged surface capable of supporting EOF, as discussed above. Because they are highly crosslinked the polymer monoliths produced by the method described herein are extremely stable. They neither swell nor are dissolved when exposed to a wide variety of solvents among them being 100% acetonitrile, 100% tetrahydrofuran, and aqueous solutions having pHs ranging from 2–12, and mixtures thereof. Moreover, the polymer monolith can be extracted with boiling methanol and air dried without suffering structural degradation. The invention further provides for the use of polymerization solvent compositions that possess conductivities that are at least about 0.4 mho/cm and thus can be easily removed after completion of the polymerization step by EOF. Included among these solvents are $C_1$–$C_4$ alcohols, $C_4$ ethers, $C_3$–$C_6$ esters, $C_1$–$C_4$ carboxylic acids, methyl sulfoxide, sulfolane, N-methyl pyrrolidone, and aqueous buffers (pH 2–12) and mixtures thereof. A particularly preferred solvent is a mixture of 60 vol % acetonitrile, 20 vol % ethanol, and 20 vol % 5 mM phosphate buffer pH 6.8. Polymerization solvents having conductivities of this magnitude can support currents as high as 0.1 $\mu$A/kV and thus fluid flowrate of about 1 mm/sec at field strengths of 200–300 V/cm. At this flowrate the full fluid volume of a column 100 $\mu$m in diameter and 30 cm long can be completely exchanged in 5 min.

The following examples illustrate generally methods for preparing monolithic polymer materials in capillaries and microchannels and removing the conducting polymerization solvent by EOF, in accordance with the present invention. These examples only serve to illustrate the invention and are not intended to be limiting. Modifications and variations may become apparent to those skilled in the art, however these modifications and variations come within the scope of the appended claims. Only the scope and content of the claims limit the invention.

EXAMPLE 1

Equal weights of 2,2'-azobisisobutyronitrile (AIBN) and 2-acrylamido-2-methyl-1-propanesulphonic acid (AMPS) were dissolved in a polymerization solvent comprising about 20 vol % EtOH, 60 vol % MeCN, and 20 vol % 5 mM phosphate buffer (pH 6) to form a monomer solution. Finally, 300 μL of 1,3-butanediol diacrylate (BDDA), 685 μL of butyl acrylate, and 3 μL of Z-6030 (Z-6030 is the tradename of an adhesion promoter obtained from Dow Chemical) were added to the mixture.

Prior to filling a capillary with the solution described above, the walls of the capillary were pretreated. The purpose of this pretreatment step is to functionalize the silica wall of the capillary so that the polymer monolith will be covalently linked to the wall. To provide a negative charge to the capillary walls, the capillary was flushed with a solution of z-6030 (obtained from Dow Corning Co.) (20 vol %), glacial acetic acid (30 vol %) and deionized water (50 vol %). In order to provide a positive charge to the capillary walls, z-6030 in the pretreatment mixture was replaced with N-[3-(trimethoxysilyl)propyl]-N'-(4-vinlbenzyl)ethylene diamine hydrochloride. Following the pretreatment step, the capillary was rinsed with deionized water and pressurized nitrogen was used to force the monomer solution, which had been degassed under vacuum, into the capillary. Subsequently, the monomer was polymerized by exposure to UV radiation.

The polymerization solvent can now be exchanged for a running buffer by EOF. By way of example, the polymerization solvent was completely exchanged for a running buffer consisting of a 70:30 mixture of MeCN and 5 mM phosphate solution (pH 6.8) by applying a voltage of between 2 and 3 kV for about 5 minutes. Currents of about 2 to 3 μA were measured during the exchange process. It is preferred that unreacted monomeric materials be removed from the polymer monolith prior to exchanging for a running buffer. This can be accomplished by using EOF to flush the polymer monolith with a solution that contains a higher concentration of organic solvent.

Figure 2:
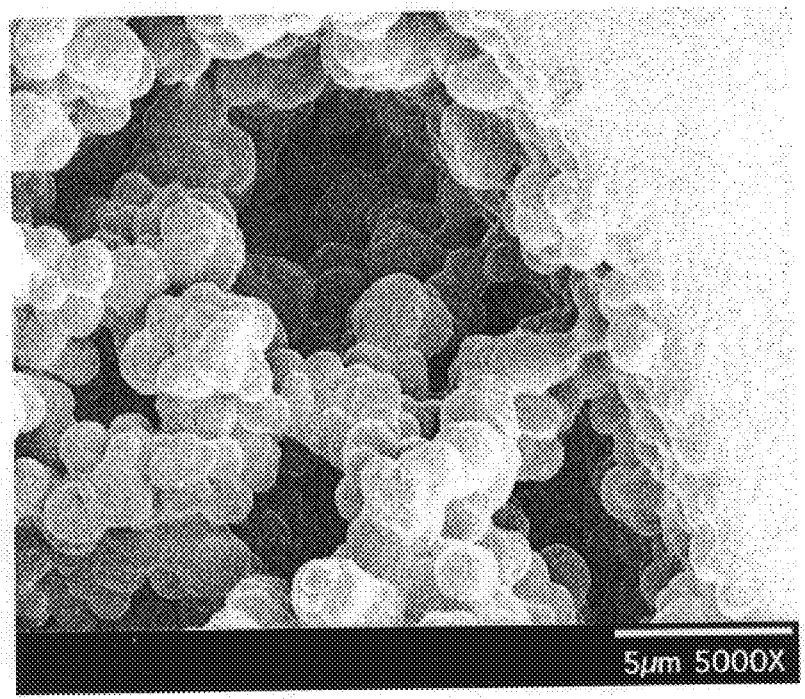
FIG. 2 is a higher magnification of FIG. 1 showing binding of the polymer material to the capillary walls.

The microstructure of a porous polymer material produced by the invention is shown in FIG. 1. This material, produced by polymerization of acrylate monomers, is contained within a 100 μm diameter capillary. FIG. 2 shows the binding of the porous polymer material to the walls of the capillary.

EXAMPLE 2

A single phase solution was made from a 2:1 volumetric ratio of polymerization solvent to monomer. The solvent comprised a mixture of 20 vol % EtOH, 60 vol % MeCN, and 20 vol % 5 mM phosphate buffer (pH 6). The monomers were a mixture of [2-(methacryloyloxy) ethyl] trimethyl ammonium methyl sulfate, tetraethyleneglycol diacrylate, and methacrylonitrile in the volumetric ratio 5:24:71. An amount of AMPS equivalent to 5 wt % of the monomers was added to the monomer solution.

The monomer solution was treated as above and injected into a capillary under nitrogen pressure. The monomers were thermally polymerized by heating to 65° C. for about 12 hrs. The polymerization solvent was removed from the resulting polymer monolith and exchanged for a running buffer, comprising an 80:20 mixture (by volume) of a 5 mM acetate buffer and 1-propanol, by applying a voltage of about 1–2 kV for about 12 to 24 hrs. During the exchange currents of 0.4 to 4 μA were measured. The inventor has found that by increasing the amount of charged monomer the exchange current can be correspondingly increased.

As discussed above, it is preferred that prior to incorporation of a running buffer any unreacted monomer material be removed by using EOF to purge the polymer microstructure with a high organic solution, i.e., a solution that is composed of water and an organic solvent, wherein the concentration of water is less than about 50 vol %.

EXAMPLE 3

A clear solution was prepared by dissolving a monomer mixture composed of 30:33:35:2 vol % ethylene glycol, butyl methacrylate, tetrahydrofurfuryl methacrylate, [2-(methacryloyloxy) ethyl] trimethyl ammonium methyl sulfate in the polymerization solvent set forth above. An amount of AMPS equivalent to 5 wt % of the monomers was added to the monomer solution. The monomer solution was degassed, injected into a capillary under nitrogen pressure, and thermally polymerized using AIBN as an initiator.

As before, the polymerization solvent was exchanged for a buffer solution by applying a voltage to the polymer monolith and removing the polymerization solvent by EOF. It has been found that conductivities similar to that of a 0.1 M phosphate buffer solution could be achieved with currents typically in the range of 10–50 μA/kV.

In each of the examples above the ratio of polymerization solvent to monomer was about 67:33.

Mercury porosimetry, BET surface area analysis and electron microscopy were used to characterize the materials produced in the examples above, such as that shown in FIG. 1. Structure characterization was done on bulk material that has been extracted with boiling methanol, air dried and placed under a vacuum. While the material characterized was not a direct representation of the state of the material under chromatographic conditions, these highly crosslinked hydrophobic polymers do not swell appreciably when filled with chromatographic solvents nor do they shrink upon boiling methanol extraction. Also, in studies of many similar materials we find no difference in the extracted structures when liquid methanol or supercritical $CO_2$ is used for the extraction.

Figure 3:
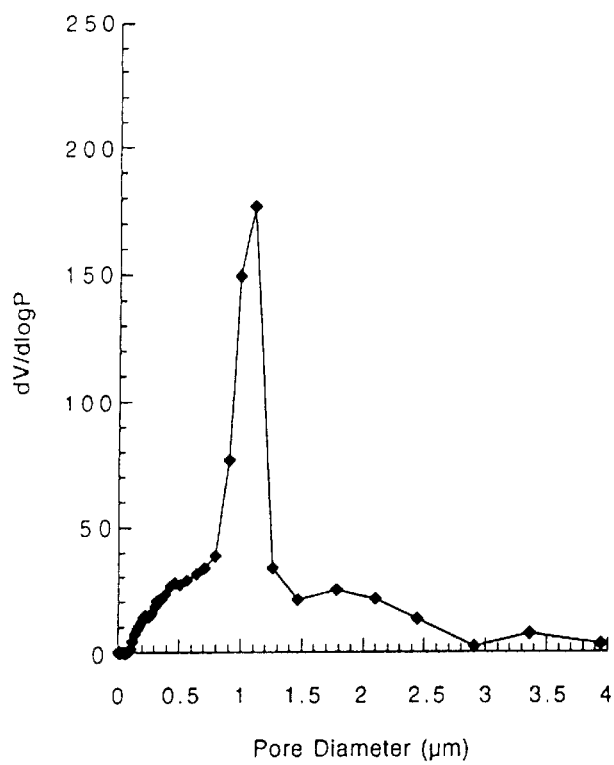
FIG. 3 shows a typical pore size distribution of the polymer material.

SEM micrographs (FIG. 1) indicate that the polymer material produced by the invention is composed of linked nodules that are about 1 μm in diameter. The polymer monoliths have surface areas of about 1–3 $m^2/g$, which argues against the existence of extensive nanopores in their structures. The theoretical surface area for 1 $g/cm^3$ spheres of diameter 1 μm at a material density of 0.4 is 3 $m^2/g$. The materials produced by the present invention are very close to the theoretical number considering that the polymer nodules are not spherical and overlap considerably. While peak pore diameters are centered around 1 μm there is clearly a distribution of pore sizes (FIG. 3). The pore size and polymer nodule size do not necessarily have any relationship, but in phase separated structures such as these, a correlation of nodule size, surface area and pore size is often observed.

Figure 4:
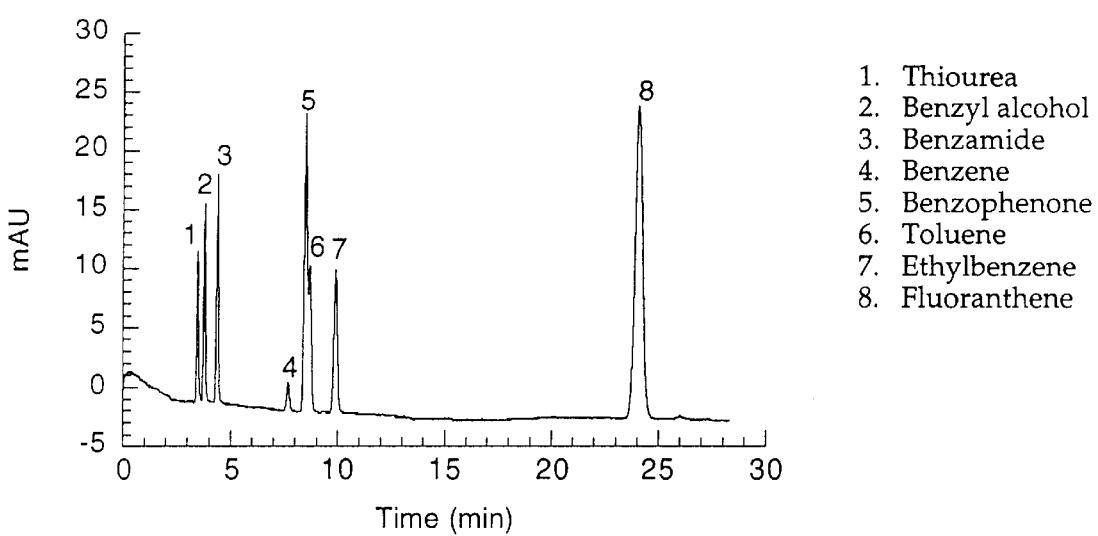
FIG. 4 shows separation of a set of 8 analytes in 70/30 MeCN/ 5 mM tris pH 8 at a field strength of 231 V/cm.

To evaluate the effectiveness of the porous polymer materials of the invention as chromatographic separation media, a formulation comprising 70 vol % butyl acrylate, 30 vol % crosslinker, and 0.5 vol % charged monomer was prepared as above. The porous polymer product, which had a average pore size of about 1.1 µm, was used as the separation medium in a reverse-phase capillary electrochromatographic separation. A mixture of 8 neutral analytes was injected onto the column and subjected to a field strength of about 230 V/cm. The result of the separation is shown in FIG. 4. Smaller ring aromatics were eluted within about 10 minutes of injection with the larger fluoranthrene taking an additional 15 minutes to elute. It should be noted that these results are comparable with those of Peters et al., Anal. Chem., 69, 3646–3649, 1997, who used a methacrylate column. However, the separations could be accomplished at a relatively low field strength of about 230 V/cm using the porous polymer medium prepared by the inventive method as opposed to a field strength of greater than 800 V/cm required by the methacrylate column.

In summary, by combining porous polymer materials that incorporate charged species in their structure and thereby support a double layer with a polymerization solvent having a conductivity of at least about 0.4 mho/cm it now possible to use electroosmotic flow to easily and efficiently remove the polymerization solvent from polymer monoliths prepared by phase separation. The step of removal can incorporate replacing the polymerization solvent with a running buffer solution for application to chromatography and electrokinetic pumping. Extensive crosslinking allows the porous polymer monoliths to achieve high molecular weights and, in contrast to prior art porous polymer materials imparts a high structural stability such that the polymer monolith resists swelling and/or dissolution in the presence of a wide variety of organic and aqueous liquids and can be air dried.

The foregoing is intended to be illustrative of the present invention and are not to be construed as a limitation or restriction thereon, the invention being delineated in the following claims.

I claim:

1. A method for producing a highly crosslinked porous cast-to-shape polymer structure in capillaries, the method comprising:

preparing a mixture of monomers in a polymerization solvent, wherein the monomers include bifunctional monomers, and wherein the polymerization solvent has a conductivity of at least about 0.4 mho/cm;

filling the capillary tube with the monomer mixture;

polymerizing the monomers; and exchanging the polymerization solvent for a conducting liquid that can be a buffer solution by applying an electric field to the polymer.

2. The method of claim 1, wherein the polymerization solvent is selected from the group including $C_1$–$C_4$ alcohols, $C_4$ ethers, $C_3$–$C_6$ esters, $C_1$–$C_4$ carboxylic acids, methyl sulfoxide, sulfolane, N-methyl pyrrolidone, and 35 vol % aqueous buffers and mixtures thereof.

3. The method of claim 2, wherein the polymerizing solvent is a mixture of 60 vol % acetonitrile, 20 vol % ethanol, and 20 vol % 5 mM phosphate buffer pH 6.8.

4. The method of claim 1, wherein the monomers are acrylate monomers.

5. The method of claim 4, wherein the monomers include bifunctional monomers selected from the group including sulfonates, phosphonates, and boronates and ammonium compounds containing active vinyl groups in the molecule.

6. The method of claim 1, wherein the step of polymerizing is by UV radiation.

7. The method of claim 1, wherein the volume ratio of polymerization solvent to monomer is about 67:33.

8. A porous polymer material made by the method of claim 1.

9. The polymer material of claim 8, wherein the surface area is between about 1–3 $m^2$/g.

10. The method of claim 1, further including the step of pretreating the walls of a capillary.

* * * * *